US00PP10258P

United States Patent [19]

Cosner et al.

[11] Patent Number: Plant 10,258

[45] Date of Patent: Feb. 24, 1998

[54] DOUBLE IMPATIENS PLANT NAMED 'TIOGA LIGHT PINK'

[76] Inventors: Harlan B. Cosner; Sue L. Cosner, both of P.O. Box 173, Broadbent, Oreg. 97414

[21] Appl. No.: 772,494

[22] Filed: Dec. 23, 1996

[51] Int. Cl.[6] ..... A01H 5/00

[52] U.S. Cl. ..... Plt./87.6

[58] Field of Search ..... Plt./87.6

*Primary Examiner*—James R. Feyrer

*Attorney, Agent, or Firm*—C. A. Whealy

[57] ABSTRACT

A new and distinct cultivar of Double Impatiens plant named 'Tioga Light Pink', characterized by its large light pink flowers; flowers held above or beyond the foliage; consistently double and symmetrical flower form; numerous flowers per plant; freely branching, dense plant habit; upright and slightly arching plant habit, plants almost spherical; and medium green foliage.

1 Drawing Sheet

The present invention relates to a new and distinct cultivar of Double Impatiens plant, botanically known as *Impatiens walleriana*, and hereinafter referred to by the cultivar name 'Tioga Light Pink'.

The new cultivar is a product of a planned breeding program conducted by the inventors in Coquille, Oreg. The objective of the breeding program was to develop varieties with attractive flower colors, consistently double flower form, uniform plant habit, and numerous flowers per plant.

The new cultivar originated from a cross made in August, 1991, by the inventors of an unnamed proprietary seedling selection as the male or pollen parent with an unnamed proprietary seedling selection as the female or seed parent.

The cultivar 'Tioga Light Pink' was discovered and selected by the inventors as a flowering plant within the progeny of the stated cross in a controlled environment in Coquille, Oreg. Asexual reproduction of the new cultivar by terminal cuttings taken at Coquille, Oreg., has shown that the unique features of this new Double Impatiens are stable and reproduced true to type in successive generations of asexual reproduction.

The following traits have been repeatedly observed and are determined to be the unique characteristics of 'Tioga Light Pink'. These characteristics in combination distinguish the new Double Impatiens as a new and distinct cultivar:

1. Large light pink flowers.
2. Flowers held above or beyond the foliage.
3. Consistently double and symmetrical flower form.
4. Numerous flowers per plant.
5. Freely branching, dense plant habit.
6. Upright and slightly arching plant habit, plants almost spherical.
7. Medium green foliage.

In contrast to plants of the new Double Impatiens, plants of the parent proprietary seedling selections have semi-double flowers with reproductive organs and capable of producing seed. In addition, the male parent has white-colored flowers and is taller than the new Double Impatiens; and the female parent has darker pink colored-flowers than the new Double Impatiens.

The new Double Impatiens is similar in flower color to the Double Impatiens cultivar Rosebud White (not patented). However in side-by-side comparisons in Coquille, Oreg., under commercial practice, plants of the new Double Impatiens differed from plants of the cultivar Rosebud White in the following characteristics:

1. Plants of the new Double Impatiens are taller and more vigorous than plants of the cultivar Rosebud White.
2. Plants of the new Double Impatiens are more freely branching and are denser than plants of the cultivar Rosebud White.
3. Leaves of plants of the new Double Impatiens are longer than leaves of plants of the cultivar Rosebud White.
4. Flowers of plants of the new Double Impatiens face upward or outward whereas flowers of plants of the cultivar Rosebud White face outward or downward as peduncles of plants of the cultivar Rosebud White are weaker than peduncles of the new Double Impatiens.
5. Plants of the new Double Impatiens are more freely flowering than plants of the cultivar Rosebud White are light green in color.

A detailed comparison of plants of the new Double Impatiens and the cultivar Rosebod White appears in Chart A at the end of the specification.

The new Double Impatiens has not been observed under all possible environmental conditions. The phenotype may vary significantly with variations in environment such as temperature and light level, without, however, any variance in genotype.

The accompanying colored photographs illustrate the overall appearance and flower color of the new Double Impatiens, showing the colors as true as it is reasonably possible to obtain in colored reproductions of this type.

The first photograph comprises a side perspective view of a typical plant of the new Double Impatiens.

The second photograph comprises a side perspective view of typical plants of the cultivar Rosebud White (left) and the new Double Impatiens (right) showing the differences in plant and flowering habit. Flower and foliage colors in the photograph may appear different from the actual colors due to light reflectance.

The following observations, measurements, values, and comparisons describe plants grown in Coquille, Oreg., grown under double layer of polyethylene with day temperatures ranging from 23 to 30C and night temperatures ranging from 10 to 18C, and light levels ranging from 3,000 to 5,000 footcandles.

In the following description, color references are made to The Royal Horticultural Society Colour Chart except where general terms of ordinary dictionary significance are used.

Botanical classification: *Impatiens walleriana* cultivar 'Tioga Light Pink'.

Parentage:

*Male or pollen parent.*—Unnamed proprietary seedling selection.

*Female or seed parent.*—Unnamed proprietary seedling selection.

Propagation:

*Type cutting.*—Terminal cuttings.

*Time to initiate roots.*—About 14 days at a temperature of 20C.

*Rooting habit.*—Numerous, fibrous, and well-branched.

Plant description:

*Form.*—Upright and slightly arching, rounded, almost spherical.

*Growth habit.*—Vigorous. Dense and bushy growth. Flowers above or beyond the foliage. Suitable for 10 to 25-cm containers.

*Plant height.*—About 30 cm.

*Branching habit.*—Freely branching with about seven lateral branches, branches strong.

*Lateral branches.*—Size: Length: About 25 cm. Diameter: About 1 cm. Internode length: About 3.5 cm. Color: 145A.

*Foliage description.*—Leaves simple, generally symmetrical, abundant, alternate, and flat in aspect. Size, largest leaves: Length: About 7 cm. Width: About 3.5 cm. Shape: Ovate with acuminate apex, attenuate base and crenate margin. Texture: Smooth. Color: Upper surface: 137A. Lower surface: 147B. Venation, upper surface: 147B. Venation, lower surface: 147B. Petiole: Size: Length: About 2 cm. Diameter: About 2.5 mm. Color: White to light green.

Flower description:

*Flower type and habit.*—Large light pink flowers. Consistently double and symmetrical flowers. Freely and continuously flowering. Flower buds open similar to a rose in fullness. Flowers arise from leaf axils, terminal bud opening first. Usually eight flowers per lateral branch. Flowers positioned above or beyond the foliage and face upward or outward. Flowers self-cleaning.

*Time to flower.*—Flowering generally commences four to six weeks after planting.

*Flowering season.*—Year-round under greenhouse conditions. In the garden, flowering is continuous from spring until fall.

*Flower diameter.*—About 3.5 cm.

*Flower depth (height).*—About 1.5 cm.

*Flower buds.*—Size: Length: About 1.5 cm. Diameter: About 1.1 cm. Shape: Ovoid. Color: 69A.

*Petals/petaloids.*—Quantity: Numerous. Size (largest petals): Length: About 1.7 cm. Width: About 1.75 cm. Shape: Round with rounded apex, cuneate or obtuse base and entire margin. Texture: Satiny, smooth. Color: When opening, upper surface: Iridescent, 65A/65B. When opening, lower surface: Iridescent, 69A. Mature, upper surface: Iridescent, 69A. Mature, lower surface: Iridescent, 69A. Fading to: Iridescent, 69A.

*Spur.*—Length: About 2.5 cm. Shape: Narrow and curved. Color: Light green.

*Peduncles.*—Length: About 2 cm. Angle: Upright to outwardly arching. Strength: Moderate. Color: 145A.

*Reproductive organs.*—None observed. Under optimal flowering conditions, reproductive organs are not observed as these structures develop into sterile petaloids. Without the development of functional reproductive organs, pollination and subsequent seed production are not observed.

Disease resistance: Under commercial conditions, resistance nor susceptibility to pathogens has not been observed.

CHART A

| CHARACTERISTIC | TIOGA LIGHT PINK | ROSEBUD WHITE |
|---|---|---|
| PLANT HEIGHT | About 30 cm | About 26 cm |
| VIGOR | Vigorous | Moderate |
| BRANCHING HABIT | Moderate to freely, usually 7 lateral branches per plant, dense | Low to moderate, usually 5 lateral branches per plant, less dense |
| LATERAL BRANCH LENGTH | About 25 cm | About 19 cm |
| LEAF LENGTH | About 7 cm | About 6 cm |
| LEAF WIDTH | About 3.5 cm | About 3.5 cm |
| FLOWERING HABIT | Flowers face upward or outward | Flowers face outward or downward |
| QUANTITY OF FLOWERS PER LATERAL BRANCH | About 8 | About 5 |
| FLOWER DIAMETER | About 3.5 cm | About 3 cm |
| PEDUNCLE ANGLE | Upright to outwardly arching | Outwardly arching to downward |
| PEDUNCLE STRENGTH | Moderate | Weaker |

It is claimed:

1. A new and distinct Double Impatiens plant named 'Tioga Light Pink', as illustrated and described.

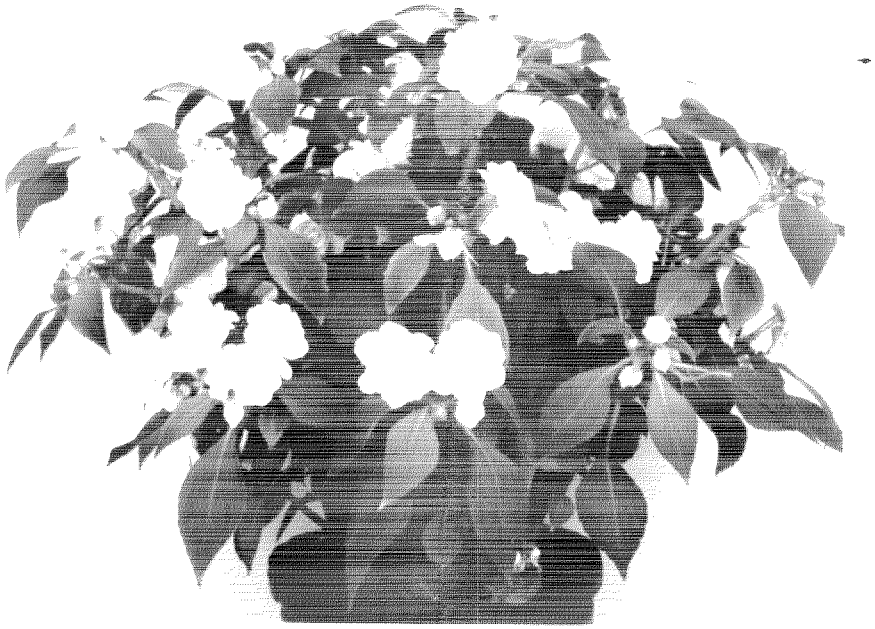
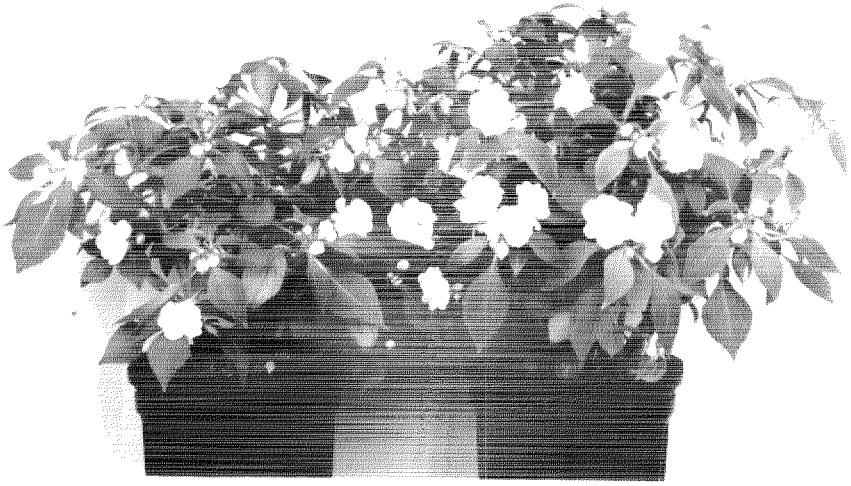

* * * * *